United States Patent
Wang et al.

(10) Patent No.: US 8,456,178 B2
(45) Date of Patent: Jun. 4, 2013

(54) METHOD AND DEVICE FOR INDUCTIVE CONDUCTIVITY MEASUREMENTS OF A FLUID MEDIUM

(75) Inventors: Changlin Wang, Shanghai (CN); Fengjin Wang, Shanghai (CN); Xiaokai Wang, Shanghaus (CN); Jürgen Ammann, Zürich (CH)

(73) Assignee: Mettler-Toledo AG, Greifensee (CH)

( * ) Notice: Subject to any disclaimer, the term of this patent is extended or adjusted under 35 U.S.C. 154(b) by 359 days.

(21) Appl. No.: 13/006,154

(22) Filed: Jan. 13, 2011

(65) Prior Publication Data
US 2011/0140717 A1 Jun. 16, 2011

Related U.S. Application Data

(63) Continuation of application No. PCT/EP2009/005077, filed on Jul. 13, 2009.

(30) Foreign Application Priority Data

Jul. 14, 2008 (CN) .......................... 2008 1 0040545

(51) Int. Cl.
*G01R 27/28* (2006.01)
*G01R 27/08* (2006.01)
(52) U.S. Cl.
USPC .......................................... 324/654; 324/691
(58) Field of Classification Search
USPC ................. 324/654, 649, 600, 522, 527, 439, 324/445, 446, 722, 76.75, 207.15, 691
See application file for complete search history.

(56) References Cited

U.S. PATENT DOCUMENTS

| | | | |
|---|---|---|---|
| 2,542,057 A * | 2/1951 | Relis | 324/445 |
| 4,220,920 A | 9/1980 | Gross | |
| 5,455,513 A * | 10/1995 | Brown et al. | 324/445 |
| 5,612,622 A | 3/1997 | Goldman et al. | |
| 5,767,682 A | 6/1998 | Sekimoto et al. | |
| 2005/0116724 A1* | 6/2005 | Red'ko et al. | 324/649 |
| 2010/0207643 A1* | 8/2010 | Eberheim et al. | 324/654 |
| 2010/0295558 A1* | 11/2010 | Eberheim et al. | 324/654 |
| 2011/0001490 A1* | 1/2011 | Eberheim et al. | 324/654 |

FOREIGN PATENT DOCUMENTS

DE 4137422 A1 5/1993

OTHER PUBLICATIONS

Inductive Conductivity and Concentration Meter, Control and Instruments in Chemical Industry, 1997, pp. 56-58, 24(1).

\* cited by examiner

*Primary Examiner* — Hoai-An D Nguyen
(74) *Attorney, Agent, or Firm* — Standley Law Group LLP

(57) ABSTRACT

Exemplary embodiments of the present invention include methods and devices for the electromagnetic (inductive) measurement of the conductivity of liquids by immersing a sensor into the liquid, wherein the sensor includes at least 2 toroidal cores, one of said cores carrying an excitation coil and the other core carrying an induction coil. Exemplary methods include converting the induced current at the induction coil into an alternating square-wave voltage, followed by rectification. A sample-hold circuit may be employed to avoid the transition time of the alternating square-wave current conversion. The demodulated DC voltage is proportional to the conductivity of the measured liquid.

17 Claims, 3 Drawing Sheets

METHOD AND DEVICE FOR INDUCTIVE CONDUCTIVITY MEASUREMENTS OF A FLUID MEDIUM

CROSS-REFERENCE TO RELATED APPLICATIONS

This application is a continuation under 35 USC §120 of PCT/EP2009/005077, filed on 13 Jul. 2009 which is, in turn, entitled to, and claims, benefit of a right of priority under 35 USC §119 from Chinese Patent Application No. 200810040545.X, filed on 14 Jul. 2008. The content of each of these applications is incorporated by reference as if fully recited herein.

TECHNICAL FIELD

Exemplary embodiments of the present invention include methods and devices for electromagnetically or inductively measuring the electrical conductivity of a fluid medium, in particular a liquid or a solution. It belongs to the technical field of measurement instruments.

BACKGROUND

The electrical conductivity of a liquid is an important analysis parameter of electrochemistry. Its measurement has a wide application in fields like the chemical industry, metallurgy, biology, medicine, grain testing, water conservancy, energy resources, etc. Conductivity measuring methods can be divided into 2 groups: contact-type and non-contact type.

A non-contact type measurement applies the principle of electromagnetic induction and is therefore also referred to as an electromagnetic conductivity-measuring method or an inductive conductivity-measuring method. As there is no contact between the conductive part of the measuring component and the measured liquid, sensors of this type possess the advantages of good solidity, corrosion resistance, non-polarization and long service life. There has been a long history of development since the basic principle of electromagnetic measurement of the conductivity of a liquid was invented and applied in practice.

For example, U.S. Pat. No. 2,542,057 to M. J. Relis opened the basic theory to the public in 1951. The sensor according to this reference employs a pair of coaxial toroidal cores which are covered by corrosion-protective and electrically insulating material. The inner hole of the 2 toroidal cores allows the current path through the liquid. According to the electromagnetic induction principle, when an alternating current is sent through the excitation coil, an alternating magnetic flux is generated in the exciting toroidal core, which in turn generates an induction current through the loop in the measured liquid. The induction current generated in the loop presents itself as a current loop which crosses both the exciting toroidal core and the pick-up toroidal core. This current loop generates an alternating magnetic flux in the toroidal core, which generates in the induction coil an induced current, which in turn produces an induced electrical voltage at the induction coil.

Because the induction current of the liquid is related to its conductivity, the induced current and the induced voltage of the induction coil (open-circuit voltage) is proportional to the current through the liquid. Thus, the conductivity of the liquid can be derived from the measurement of the induced current or the induced voltage. The conductivity G of the liquid is calculated from the formula $G=C/R$, wherein C is the sensor cell constant and R is the equivalent resistance of the loop through the liquid. In the past, the excitation voltage was usually an AC sine-wave, and the induced voltage of the induction coil was measured by an electric bridge-balancing method, which had the disadvantages of low precision and a low level of automation. At present, due to the development of modern electronic technologies, this method is rarely used.

The method of measuring the induction voltage is relatively simple and is still being used. For example, according to the method which was introduced in the publication "Inductive Conductivity and Concentration Meter", *Chemical Automation and Meters*, 1997, 24(1): 56-58, the induction current of the liquid is related to its conductivity. The induced current or the induced voltage (open-circuit voltage) of the induction coil is proportional to the current through the liquid. Hence, the conductivity of the liquid can be derived from the measurement of the induced current or the induced voltage of the induction coil. But in this method, the induced voltage of induction coil is not only related to the conductivity of the liquid, but also to the inductance of the excitation coil, which negatively affects the linearity of the measurement. Also, the magnetic permeability of the toroidal core is affected by temperature and other factors, which causes a temperature-dependent drift of the inductance of the excitation coil and has a negative effect on the precision of the measurement.

To increase the accuracy of the measurements U.S. Pat. No. 5,455,513 A1 to Neil L. Brown proposes a system, which employs a current-compensation method, also known as zero-current method. Thereby the induced current of the induction coil is balanced by an additional compensation such that the compensation current is subtracted from the induction current to produce a zero-current and a corresponding zero-voltage. This is a method of relatively high precision, because when the voltage at the measurement terminal of the induction coil is zero, the induced current in the induction coil is proportional to the conductivity of the liquid. However, this method is relatively complicated and costly, because it involves the steps of pre-amplification, tuned filter amplification, in-phase detection, integration, switching multiplication and further amplification to generate the appropriate compensation current. Further, to change the measurement range, it is usually necessary to change the parameters of all the involved components. Also for the integration step mentioned above, a high quality integration capacitor is required, and therefore the cost is high.

SUMMARY OF THE INVENTION

In view of the aforementioned disadvantages of the existing device for the electromagnetic and inductive measuring of the conductivity of a liquid, an objective of exemplary embodiments of the present invention is to overcome the drawbacks of the prior art, in particular to provide a simple and high-accuracy measuring method and a corresponding measurement device. A further objective of exemplary embodiments is to improve the adaptability to different measurement ranges.

The technical solution is provided by a measurement method and a measurement device, which comprise the features described in the independent claims. Further embodiments of the invention are disclosed in the additional dependent claims.

Exemplary embodiments according to the present invention include a method for inductively measuring the electrical conductivity of a fluid medium with a sensor, which comprises an excitation coil for applying an excitation current to the fluid medium and an induction coil for receiving an inducted current generated by the excitation current via the fluid medium, said method comprising the following steps: applying to the excitation coil an alternating excitation current; measuring the induced current to provide a measurement signal corresponding to the induced current; providing the measurement signal to a sample-hold process to produce the output signal, wherein the sample-hold process holds the measurement signal at a substantially constant value during a hold time period (H), which is synchronized to the alternating excitation current and configured long enough to obtain a substantially stable signal and/or a signal, which is substantially unaffected by effects introduced by the direction change of the alternating current or time-dependent transitions of the measurement signal and/or that the duration of hold time period (H) is approximately longer than a quarter of the time period of the alternating current; and providing the output signal for computing the conductivity of the fluid medium.

With this exemplary method high-accuracy measurements are achieved by suppressing disturbing effects, which negatively affect the measurement or the linearity of the conductivity measurement. Furthermore the use of a sample-hold process allows the building a simple, very cost-effective forward circuit with a few electrical components like an input circuit, an amplifier and a sample-hold circuit. In particular a costly, high quality integration capacitor can be avoided. In addition, the measurement circuit can easily be adapted to different measurement ranges by changing a few components, in particular by changing the gain of a single amplifier.

With exemplary methods and devices according to the invention, a large number of negative effects can be reduced or eliminated, which negatively affects the measurement or the linearity of the measurement, in particular effects of the inductance of the excitation coil, effects of an amplification circuit or a rectification circuit and especially effects of the length of the cables. Also, the magnetic permeability of the toroidal core is affected by temperature and other factors, which causes a temperature-dependent drift of the inductance of the excitation coil and has a negative effect on the precision of the measurement. Never the less, with the sample-hold process these influences and disturbing factors can effectively be suppressed. Therefore the present invention discloses a method and a device for electromagnetically (inductively) measuring the conductivity of liquids, wherein the method and the device are distinguished by their simplicity and high accuracy.

Further the sample-hold process has the advantage that it bridges transitions, during which an over-shooting or an over-damping of the signal occurs, which has a detrimental effect on the precision of the measurement. According to the invention, the impact of these transitions is avoided to optimize the measurement precision. The duration of the hold time period is configured long enough to obtain a substantially stable signal and/or a signal, which is substantially unaffected by effects introduced by the direction change of the alternating current or time-dependent transitions of the measurement signal and/or that the duration of hold time period is approximately longer than a quarter of the time period of the alternating current. Further it is very cost-effective to use a sample-hold circuit to avoid the transition time of the polarity change of the alternating square-wave signal.

This hold time period has the advantage that it also bridges those transitions, during which the polarity of the alternating excitation current and/or the corresponding measurement signal changes. These transitions are very complex, because of many influencing factors like impacts of the excitation circuit, capacitances of the cables, cross talk interference or dynamic characteristics of the measurement circuit, the amplification circuit or the rectification circuit. The transitions result in over-shooting and/or over-damping, which have a detrimental effect on the precision of the measurement. According to the invention, the impact of these transitions is avoided to optimize the measurement precision.

In an embodiment of the invention the excitation current and/or the measurement signal is substantially constant during a substantial period of time, in particular that it is substantially a square-wave signal. This has the advantage that these signals can be measured more precisely than other signal forms, in particular a sine-wave signal.

In another embodiment of the invention the beginning of the hold time period is approximately coincident to, in particular slightly preceding, the time of the direction change of the alternating excitation current.

In still other embodiments the hold time period is approximately larger than a quarter of the time period of the alternating current. Further it is very cost-effective to use a sample-hold circuit to avoid the transition time of the polarity change of the alternating square-wave signal.

In another embodiment of the invention prior to providing the measurement signal to the sample-hold process it is converted into a voltage and/or a digital signal and/or a rectified signal, in particular by alternating between an addition and a subtraction of the digitalized measurement signal or by inverting the sign of the digitalized measurement signal.

In the measuring step of an exemplary embodiment the rectified signal is synchronously rectified in relation to the excitation current to provide to the sample-hold process a synchronous rectified measurement signal.

In another embodiment of the invention an A/D conversion on the output signal is performed to determine the conductivity of the fluid medium and/or that the sensor is immersed into the fluid medium for measuring the conductivity of a fluid medium.

In still another embodiment of the invention the hold time period is synchronized by a timing signal, which is provided by a source of the alternating excitation current or by a control unit, which controls the source of the alternating excitation current.

Exemplary embodiments of the present invention include a method for electromagnetically (inductively) measuring the conductivity of liquids, which is performed by immersing a sensor into the liquid, wherein the sensor employs at least two toroidal cores, one of which carries an excitation coil and the other carries an induction coil. The method includes the following steps: generating an alternating square-wave voltage to supply the excitation coil; picking up the current of the induction coil; converting the current into voltage; synchronously demodulate the voltage waveform; employing a sample-hold circuit to avoid the transition time of the demodulated waveform; applying an A/D conversion on the output of the sample-hold; and computing the conductivity of the liquid based on the result of the A/D conversion.

In another embodiment of the above method for the electromagnetic (inductive) measurement of the conductivity of liquids, the terminal voltage of the output of induction coil is substantially zero.

In other embodiments of the above method for the electromagnetic (inductive) measurement of the conductivity of liquids, the method of computing the conductivity G of the liquid is calculated according to:

$$G = C/R, \text{ with } R = \frac{V_5}{I_7 N^2}$$

wherein C is the sensor cell constant, $V_5$ is the excitation voltage, N is the number of turns of the coil winding, and R is the equivalent resistance of the loop through the liquid.

In another embodiment of the above method—provided that the DC resistances of the sensor coil and the connecting cable are not so small that they can be totally ignored—the equivalent resistance of loop through the liquid is corrected as:

$$R = \frac{V_5}{I_7 N^2} - \frac{k \times (R_{L1} + R_{L2})}{N^2}$$

$R_{L1}$ is the DC resistance of the excitation coil and the connecting cable, $R_{L2}$ is the DC resistance of the induction coil and the connecting cable; k is a comprehensive coefficient with a value of 1 to 1.4. In one of the embodiments, the comprehensive coefficient k is taken as approximately 1.2.

Another embodiment of the present invention includes another method of electromagnetically (inductively) measuring the conductivity of liquids, which is performed by immersing a sensor into the liquid, wherein the sensor includes at least 2 toroidal cores, one of which carries an excitation coil and the other carries an induction coil. The method includes the following steps: supplying an alternating square-wave voltage to excite the excitation coil; picking up the current of the induction coil; converting the current into voltage; performing an A/D conversion on the voltage; alternating between addition and subtraction to realize the function of synchronous demodulation; during the alternating addition and subtraction, avoid the transition time of the A/D result; and computing the conductivity of the liquid based on the result of the operation of addition and subtraction.

Further, an exemplary embodiment of the present invention involves a measuring device for inductively measuring the electrical conductivity of a fluid medium, connectable to a sensor, which comprises an excitation coil for applying an alternating excitation current to the fluid medium and an induction coil, for receiving an inducted current generated by the excitation current via the fluid medium, said measurement device comprising an input circuit, which is connectable to the induction coil and which provides a measurement signal that corresponds to the inducted current. Thereby said measuring device comprises a sample-hold circuit with a first input connected to the input circuit to receive the measurement signal, and with a second input to receive a timing signal which corresponds to the excitation current, wherein the sample-hold circuit is operable to hold the measurement signal at a substantially constant value during a hold time period, which is synchronized to the timing signal.

In another embodiment of the measuring device, the input circuit is connected to the sample-hold circuit via an Analog-Digital-Converter and/or a rectifier, in particular a synchronous rectifier to provide to the sample-hold circuit the measurement signal, respectively as a voltage and/or a digitalized and/or a rectified and/or a synchronous rectified signal.

In still other embodiments the measuring device comprises a current source, which is connected to the excitation coil for applying the alternating excitation current, and which is connected to the sample-hold circuit for transmitting, in particular receiving or sending, the timing signal.

Exemplary embodiments of the present invention include a measuring system comprising the above measuring devise and further comprising an inductive conductivity sensor, which is operably connected to the input circuit, wherein the sensor is immersed into the fluid medium, in particular into a liquid or a solution, and/or wherein each coil of the sensor is carried by a toroidal core, in particular a ferrite ring or a magnetic ring.

In addition, other exemplary embodiments of the present invention include a device for electromagnetically (inductively) measuring the conductivity of liquids by immersing a sensor into the solution, wherein the sensor includes at least 2 toroidal cores, one of them carrying an excitation coil and the other carrying an induction coil. The device includes the following components: an excitation circuit, which generates an alternating square-wave voltage to supply the excitation coil; a current-voltage converting circuit, which converts the current of induction coil into voltage; a synchronous demodulator, which is connected to the current-voltage converting circuit to synchronously demodulate the voltage waveform; a sample-hold circuit, which is connected to the synchronous demodulator to avoid the transition time of the demodulated waveform; an A/D converter, which is connected to the sample-hold circuit to perform an A/D conversion on the output of the sample-hold; and a controller, which computes the conductivity of the liquid according to the result of the A/D conversion.

Other exemplary embodiments of the present invention include a device for electromagnetically (inductively) measuring the conductivity of liquids, wherein the measurement is performed by immersing a sensor into the solution, wherein the sensor employs at least 2 toroidal cores, one of which carries an excitation coil and the other carries an induction coil. The device includes the following components: an excitation circuit, which supplies an alternating square-wave voltage to the excitation coil; a current-voltage converting circuit, which converts the current of the induction coil into voltage; an A/D converter, which performs an A/D conversion on the output of the current-voltage converting circuit; a controller, which applies an alternating sequence of addition and subtraction to realize the function of synchronous demodulation, which during said alternating addition and subtraction avoids the transition time of the A/D output and computes the conductivity of the liquid based on the result of the alternating addition and subtraction.

Compared to the measuring circuit of the existing state of the art, an exemplary embodiment according to the present invention introduces a method with the following advantages: it uses a simpler and lower-cost circuit to precisely measure the conductivity of the liquid, even with a very long cable between the sensor and the measuring device.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Figure 1:
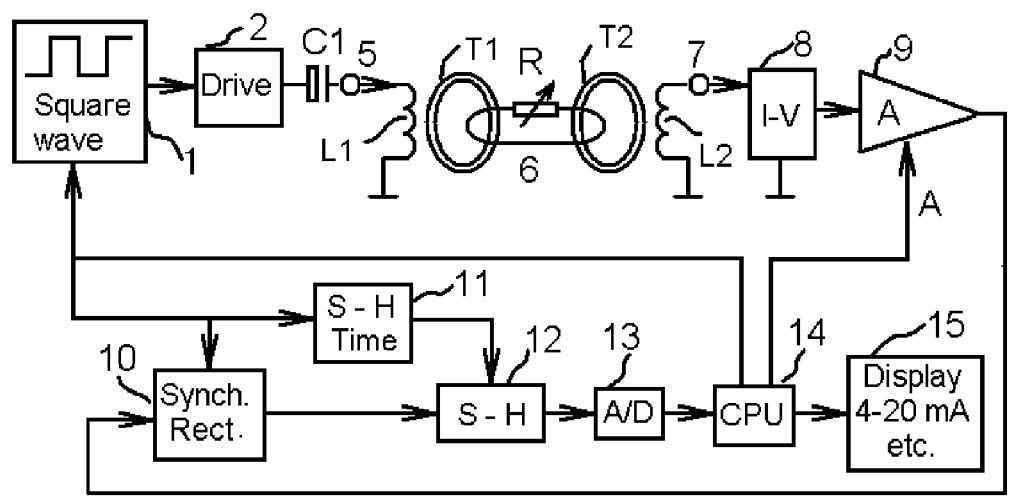
FIG. 1 is the schematic of an embodiment of the device according to the present invention and a corresponding measurement device.

FIG. 1 shows the schematic of an implementation of an exemplary method according to the present invention for the inductive measurement of the conductivity of a liquid and a corresponding measurement device. The following refers to FIG. 1, together with the main voltage waveforms in FIG. 2.

An alternating square-wave voltage 1 of a certain amplitude is supplied as the excitation voltage by the driver 2 ($V_2$) in series with a DC-blocking capacitor C1 to the excitation coil L1 of the first toroidal core T1 in the sensor. Thus, an alternating square-wave current is induced in the loop 6 in the liquid that is being measured, which is coupled to the induction coil L2 of the second toroidal core T2, and an alternating square-wave current is induced in the coil L2 and converted into an alternating square-wave voltage by an input circuit 8, which is embodied as a current-voltage (I-V) converting circuit 8. The current-voltage (I-V) converting circuit 8 ensures that the terminal voltage of the induction coil L2 is zero. By proper amplification 9 (assuming the gain is A) and a demodulation by a synchronous rectifier 10, embodied as synchronous demodulator 10 (such as rectification), the signal becomes a DC voltage. It should be noted that during rectification, a sample-hold circuit 11 and 12 is put into action to avoid the transition time of the alternating square-wave current. This DC voltage, after rectification, is proportional to the conductivity of the liquid.

It should be pointed out that the linearity is improved and the influence of the characteristics of the toroidal cores and the cables is reduced by ensuring that the terminal voltage of the induction coil L2 is zero.

According to the following analysis based on the principles of electromagnetism, if the excitation voltage is a square-wave, the terminal voltage of the induction coil L2 is zero, then the current in the liquid 6 is a square-wave and so is the current in the induction coil L2, but furthermore these currents are all proportional to the conductivity of the liquid 6, or inversely proportional to the equivalent resistance R in the loop through the liquid. C1 is a large value capacitor (for example 33 μF) which serves to suppress the DC component in the excitation coil, while for the alternating component of the excitation voltage (for example at a frequency of 5 kHz), it can be considered short-circuited. According to the electromagnetism principle:

For the excitation coil:

$$A_L\left(N^2 \frac{dI_5}{dt} - N\frac{dI_6}{dt}\right) = V_5 - I_5 R_{L1} \quad (1)$$

For the current loop in the liquid:

$$A_L\left(N\frac{dI_5}{dt} - 2\frac{dI_6}{dt} + N\frac{dI_7}{dt}\right) = I_6 R \quad (2)$$

For the induction coil (provided that the terminal voltage is zero):

$$A_L\left(N^2 \frac{dI_7}{dt} - N\frac{dI_6}{dt}\right) = -I_7 R_{L2} \quad (3)$$

Equation (3) subtracted from equation (2), having been multiplied by N gives:

$$A_L\left(N^2 \frac{dI_5}{dt} - N\frac{dI_6}{dt}\right) = I_6 R N + I_7 R_{L2} \quad (4)$$

Substitute equation (1) results in:

$$I_6 = (V_5 - I_5 R_{L1} - I_7 R_{L2})\frac{1}{RN} \quad (5)$$

In these equations, subscript 5 or L1 refers to the excitation coil; subscript 6 represents the current loop through the liquid; subscript 7 or L2 refers to the induction coil; N is the number of turns of the coil windings of the excitation coil or induction coil. It is assumed here that they have the same number of turns. If this is not the case, the formula is a slightly different, but in principle the formulas are similar. $V_5$ is the excitation voltage; or if non-ideal factors are taken into consideration, $V_5$ represents the equivalent excitation voltage; $A_L$ is related to the toroidal core, representing the inductance of a single-turn coil. $R_{L1}$ is the DC resistance of the excitation side (excitation coil L1 and connecting cable); $R_{L2}$ is the DC resistance of the measuring side (induction coil L2 and connecting cable). Considering that $R_{L1}/N^2$ and $R_{L2}/N^2$ are very small and that $I_5 R_{L1}$ and $I_7 R_{L1}$ can be disregarded in comparison to the voltage $V_5$, the following formula is very precise:

$$\text{From (5)} \quad I_6 \approx \frac{V_5}{RN} \quad (7)$$

$$\text{From (3)} \quad I_7 \approx \frac{I_6}{N} \approx \frac{V_5}{RN^2} \quad (8)$$

$$\text{Or} \quad R = \frac{V_5}{I_7 N^2} \quad (9)$$

Thus, $V_{ad} = I_7 \times R_8 \times A$ (10)

From $V_{ad}$, $I_7$ can be derived, wherein $R_8$ is the coefficient for the current-voltage (I-V) converting circuit 9; A is the gain of the voltage amplifier 9. See FIG. 3 for one embodiment of the current-voltage (I-V) converting circuit 8.

According to formula (8), if the transition time is disregarded, if $V_5$ is a square-wave, then $I_6$ is a square-wave; $I_7$ is also a square-wave and $V_{ad}$ is also a square-wave. A square-wave can generally be measured more precisely than a sine-wave.

However, in the above description, not much attention has been paid to the transition during the polarity change of the square-wave. In fact, during the transition, the situation is very complex, because the small influence of the excitation circuit, the capacitance of the cable, and also the cross talk interference, dynamic characteristics of the current-voltage converting circuit 8, the amplification circuit 9 and the rectification circuit 10 all have an impact on the transition behavior, resulting in over-shooting or over-damping, both of which have a detrimental effect on the precision of the measurement of $I_7$. According to the present invention, a sample-hold circuit 11 and 12 is arranged after the rectification to bridge the transition time of the polarity change of the alternating square-wave voltage, which optimizes the measurement precision.

Figure 2:
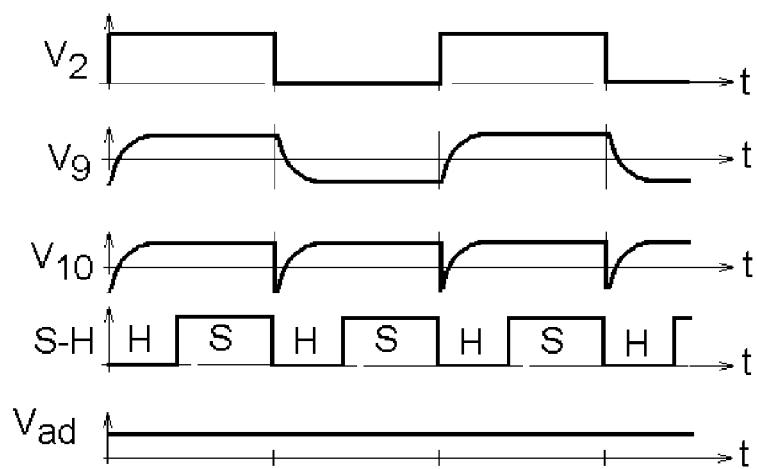
FIG. 2 illustrates the main voltage waveforms of the embodiment of FIG. 1.

FIG. 2 shows the main voltage waveforms of one embodiment of a sample-hold circuit 11 and 12. With the arrangement downstream of the rectification, it is very cost-effective to use a sample-hold circuit to avoid the transition time of the polarity change of the alternating square-wave voltage.

In the above scheme, assuming that $R_{L1}$ and $R_{L2}$ are both very small, the formulas (8), (9) and (10) can be simplified. Under normal conditions, the precision is high enough, but when the DC resistance of the sensor coils L1, L2 and the connecting cable resistance are not small enough to be ignored, they will influence the linearity of the measurement to a certain degree.

If $R_{L1}$ and $R_{L2}$ are known, a more precise correction formula is:

$$R = \frac{V_5}{I_7 N^2} - \frac{k*(R_3 + R_7)}{N^2} \quad (11)$$

wherein $$\frac{V_5}{I_7 N^2}$$

is the un-corrected equivalent resistance of the loop through the liquid being measured, R is the corrected equivalent resistance of the loop; k is the comprehensive coefficient whose theoretical value is 1, but in practice 1 to 1.4 is preferable. For example with k=1.2, the impact of the correction term can be estimated as follows: If $R_{L1}+R_{L2}$=5 ohms, N=120, and with an equivalent resistance of R≧1 ohm for the loop through the liquid, the impact of the correction term is less than 0.05%. And if $R_{L1}+R_{L2}$=10 ohms, the impact of the correction term is less than 0.1%.

Because the reciprocal of resistance is conductivity, $I_7$ is proportional to $V_{ad}$. If the correction term is extremely small, then $V_{ad}$ is proportional to conductivity. If it is not very small but is nevertheless ignored even though this would be improper, then the linearity of $V_{ad}$ and conductivity will be negatively affected. However, by applying the correction term, the linearity and precision of the measuring device can be restored to a large extent. Practically, in almost all of the measurement systems, the sum of $R_{L1}+R_{L2}$ is less than 10 ohms or even less than 5 ohms. Because the original system error is not large, the system is easily improved by applying the correction term. As the original error is not large, it is sufficient to make an approximate estimate of the sum of $R_{L1}+R_{L2}$, and to use a rough number for the comprehensive coefficient k in the estimate.

Figure 3:
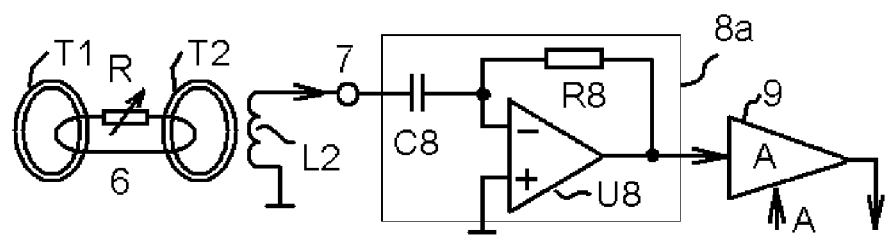
FIG. 3 illustrates an embodiment of the current-voltage converting circuit.

Shown in FIG. 3, 8a is one of the implementation examples of a current-voltage (I-V) converting circuit as presented in FIG. 1, wherein U8 is an operational amplifier. C8 is a large-value capacitor, (for example 22 µF) which can be considered as an open circuit for DC and a short circuit for audio frequency. It can prevent saturation of the output of U8 caused by the voltage offset at the input of U8. $R_8$ is a feedback resistor; the output of $U_8$ is $I_7 \times R_8$. As the negative input of U8 is at virtual ground, its potential (AC or DC) is always zero, which ensures that the terminal voltage of the induction coil L2 is zero.

Referring to the voltage waveform in FIG. 2, the voltage is amplified to the proper amplitude by the operational amplifier (V9), the gain A is controlled by CPU 14 according to the measurement range. The synchronizing rectifier 10 and excitation voltage 1 are phase-synchronized. During the negative half-cycle of the excitation voltage, the output is reversed relative to the input, otherwise the output and input equal. A sample-hold timer 11 is synchronized to the excitation voltage 1, so that when the excitation voltage 1 reverses, or shortly before reversing, a signal is sent for holding. This signal lasts for a certain time, which ensures that the transition time of the output waveform V10 of the synchronizing rectifier 10 has passed by the time of the next measuring point. A sampling signal is sent following the holding signal, which lasts till the half-wave of the excitation voltage has passed. Then the excitation voltage 1 reverses and the sample-hold timer 11 sends a holding signal again. In one embodiment, the function of the sample-hold timer 11 can be realized directly by the CPU; in another embodiment, the function of the sample-hold timer 11 can also be realized by a circuit. When the signal of the sample-hold timer 11 to the sample-hold circuit 12 calls for sampling, the output and input of the sample-hold circuit 12 are equal; when the signal of the sample-hold timer 11 to the sample-hold circuit 12 calls for holding, the output of the sample-hold circuit 12 remains the same as before. The output $V_{ad}$ of the sample-hold circuit 12 is connected to an A/D converter 13. The result of the A/D converter 13 represents the current measured in the induction coil, which is subsequently computed by CPU. At the end, the final result for the conductivity of the liquid is shown on the display 15 and made available at the 4-20 mA output, or to an alarm device, or to other devices.

In the above embodiments, because all of the effective signals are in square-wave form, and with the sample-hold circuit avoiding the transition at the beginning of every half wave, the dynamic characteristics of the excitation circuit, the cable capacitance, the dynamic characteristics of the current-voltage converting circuit, the amplification circuit and the rectification circuit have little impact on the measurement result, and especially the length of the cables has little influence on the measurement.

Figure 4:
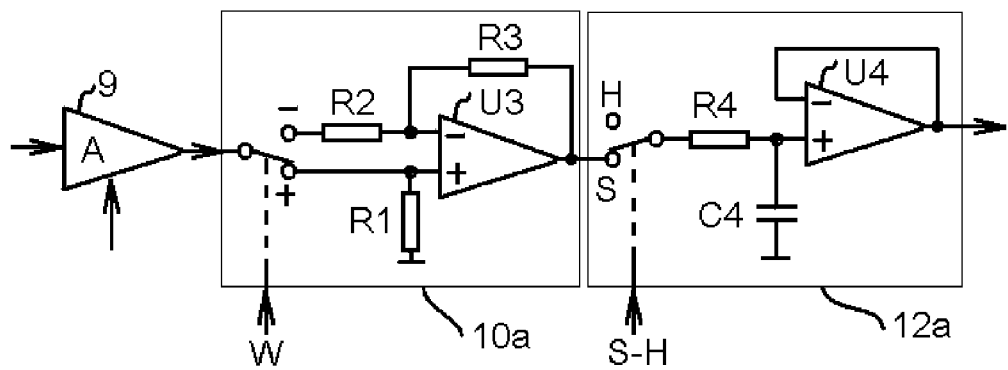
FIG. 4 illustrates an embodiment of the synchronous demodulating circuit and sample-hold circuit.

FIG. 4 illustrates an embodiment of the synchronous demodulating circuit and sample-hold circuit. Block 10a represents an implementation of the synchronous demodulation, W represents a square-wave arriving from CPU 14, identical to the square-wave signal sent to the excitation circuit. When W is high, the analog switch controlled by W is connected to "+". At this time, U3 is used as a follower, which means that the output of U3 is equal to the output of voltage amplifier 9; When W is low, the same analog switch is connected to "−". At this time, U3 is used as an inverter. With R2=R3, (wherein R2 and R3 are high-precision resistors), the output of U3 equals the output of voltage amplifier 9 multiplied by −1. Block 12a represents an implementation of a sample-hold (S-H) circuit. When the signal of the sample-hold circuit (S-H) is sampled, the analog switch controlled by W is connected to S. The output of U3 charges and discharges the capacitor C4 through the current-limiting resistor R4, which means that the voltage on capacitor C4 will follow the output voltage of U3. U4 is used as a voltage follower, whose input current is almost zero. Its output voltage equals the voltage on capacitor C4. When the signal to the sample-hold circuit (S-H) calls for holding, the respective analog switch is connected to H, so that the charging and current-limiting resistor R4 is opened and the voltage on capacitor C4 remains unchanged. The output voltage of U4 equals the output voltage on capacitor C4. In an example of an implementation, R1=30 k, R2=R3=30 k, wherein R1, R2, R3 are high-precision resistors; R4=4.7 k, C4=10 nF.

Figure 5A:
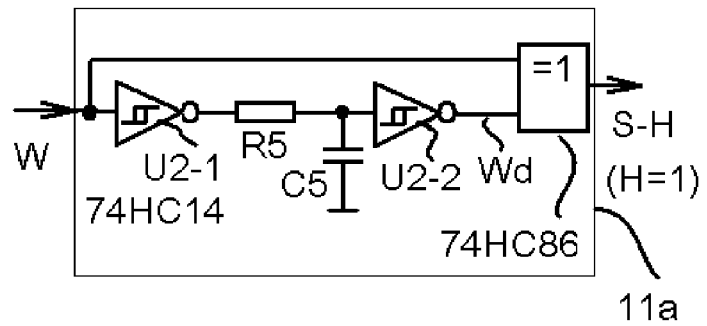
FIG. 5A illustrates an embodiment of the sample-hold timer.
Figure 5B:
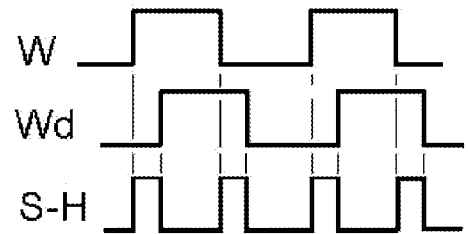
FIG. 5B is the main sequence diagram of the sample-hold timer according to FIG. 5A.

FIG. 5A and FIG. 5B show, respectively, the implementation of the sample-hold (S-H) timer and its key sequence diagram. W is a square-wave signal arriving from the CPU, which is identical to the signal sent to the excitation circuit. R5 and C5 make up a time delay circuit which equally affects the rising edge and the falling edge. Wd is always later than W by a period of time of R5×C5. Block; 74HC86 is a 2-input exclusive OR-gate. If the 2 two inputs are equal the output is 0; if the 2 inputs are not equal, the output is 1. In the S-H signal described above, 1 represents hold. Thus, at the beginning of every half wave of the excitation signal W, there is always a hold period which is followed by the "sample" signal. In an example of an implementation, R5=24 k, C5=1 nF.

In an example of an embodiment, the square-wave signal W and the S-H signal both come directly from the CPU 14. In another embodiment, the CPU 14 sends an S-H signal using a flip-flop of the type 74HC74 to divide the frequency in half in order to generate a square-wave signal W.

Figure 6:
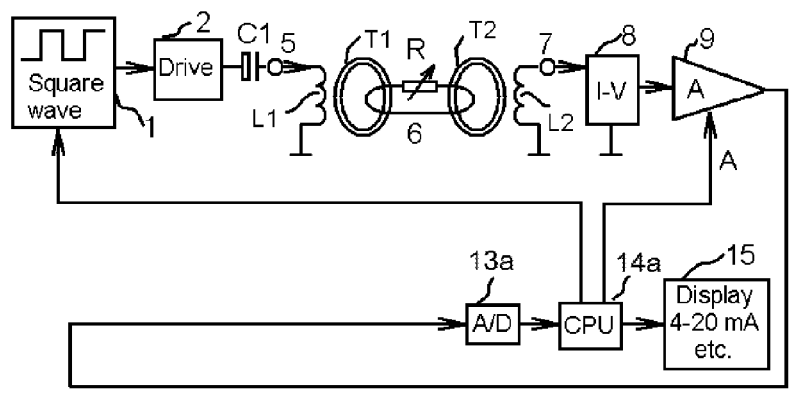
FIG. 6 is the schematic of another embodiment of the device according to this invention.

In one embodiment, the above function of synchronous demodulation, the sample-hold circuit which is used to avoid the transition time and the A/D converting circuit can also be implemented by the following solution. Referring to FIG. 6, the output voltage of amplifier 9 is sampled by a high-speed A/D converter 13a. After the sampling, the CPU applies the method of addition and subtraction to realize the function of synchronous demodulation, which means to add during the positive half cycle and to subtract during the negative half cycle, and then to obtain an average value. During the operation, the CPU only samples the A/Ds after the transition time instead of during the entire process, so as to avoid the transition time, and computes the conductivity of the liquid based on the result of the operation of addition and subtraction, using the formula (9) or (11).

In addition, the double-toroidal sensor and the measuring device could be connected by way of a cable as mentioned above. Because the conductivity of a liquid is usually related to its temperature, a temperature sensor (PT100, PT1000 or NTC) is usually included in the liquid conductivity sensor. Thus, there could be additional wires inside the cables connecting the sensor and measuring device. There could also be circuits for the temperature measurement arranged inside the measuring device, and the temperature correction could be calculated by the CPU. There could be devices against magnetic flux leakage and build-up of static charges arranged inside the sensor. Certain parameters can be calibrated for the entire system. The general principles for these methods and devices are also applicable to the exemplary methods and devices of the present invention.

The terms, symbols, expressions and examples used in the description above are not in any way meant to limit the scope of the invention, but serve only to illustrate certain aspects of the invention.

The embodiments described above only represent preferred embodiments of the present invention. Various equivalent substitutions and modifications can be made by one skilled in the art based on the foregoing description. Nevertheless, all these substitutions and modifications fall within the spirit of the present invention and the scope as defined in the following claims:

What is claimed is:

1. A method for inductively measuring the electrical conductivity of a fluid medium with a sensor, the sensor comprising an excitation coil for applying an excitation current to the fluid medium and an induction coil for receiving an induced current generated by the excitation current via the fluid medium, said method comprising:
    applying an excitation current to the excitation coil;
    measuring the induced current to provide a measurement signal corresponding to the induced current;
    providing the measurement signal to a sample-hold process to produce an output signal, wherein the sample-hold process holds the measurement signal at a substantially constant value during a hold time period synchronized to the alternating excitation current so as to obtain one of signals in a group consisting of: a substantially stable signal and a signal substantially unaffected by effects introduced by the direction change of the alternating current and time-dependent transitions of the measurement signal, wherein the duration of hold time period is approximately longer than a quarter of the time period of the alternating current;
    providing the output signal for computing the conductivity of the fluid medium.

2. The method of claim 1, wherein in at least one of the excitation current and the measurement signal is substantially constant during a substantial period of time 3. The method of claim 1, further comprising synchronizing the beginning of the hold time period to approximately coincide to the time of a direction change of the alternating excitation current.

4. The method of claim 1, further comprising converting the measurement signal into at least one of the group consisting of a voltage, a digital signal, and a rectified signal prior to being provided to the sample-hold process.

5. The method of claim 4, wherein converting the measurement signal is completed by at least one of the process selected from the group consisting of: alternating between an addition and a subtraction of a digitalized measurement signal and inverting the sign of a digitalized measurement signal.

6. The method of claim 4, further comprising synchronously rectifying the rectified signal in relation to the excitation current to provide the sample-hold process a synchronous rectified measurement signal.

7. The method of claim 1, further comprising providing a timing signal, the timing signal provided by at least one of the alternating excitation current and a control unit, wherein the control unit controls a source of the alternating excitation current.

8. The method of claim 7, further comprising synchronizing the hold time period using the timing signal.

9. The method of claim 1, further comprising:
    immersing the sensor into the fluid medium, the sensor comprising at least two toroidal cores, a first toroidal core carrying the excitation coil and a second toroidal core carrying an induction coil;
    generating an alternating square-wave voltage to supply the excitation coil;
    picking up a current of the induction coil;
    converting the current into a voltage;
    demodulating the voltage waveform synchronously;
    employing a sample-hold circuit to avoid a transition time of the demodulated waveform;
    performing an A/D conversion on the output of the sample-hold circuit; and
    computing the conductivity of the fluid medium according to the result of the A/D conversion.

10. The method of claim 1, further comprising outputting a terminal voltage from the induction coil, wherein the terminal voltage is substantially zero.

11. The method of claim 1, further comprising computing the conductivity of the fluid medium according to:

$$G = C/R \text{ with } R = \frac{V_5}{I_7 N^2}$$

wherein G is the conductivity of the fluid medium, C is a sensor cell constant, $V_5$ is an excitation voltage, N represents turns of the coil winding, and R is the equivalent resistance of a loop through the fluid medium.

12. Method according to claim 11, further comprising correcting the equivalent resistance, R, of the loop through the fluid medium according to:

$$R = \frac{V_5}{I_7 N^2} - \frac{k \times (R_{L1} + R_{L2})}{N^2}$$

wherein $R_{L1}$ is a DC resistance of the excitation coil and a connecting cable, $R_{L2}$ is a DC resistance of the induction coil and a connecting cable, and k is a comprehensive coefficient, wherein in the comprehensive coefficient is in a range between about 1 and 1.4.

13. A device for inductively measuring the electrical conductivity of a fluid medium having a sensor, the sensor includes an excitation coil for applying an alternating excitation current to the fluid medium and an induction coil for receiving an induced current generated by the excitation current via the fluid medium, the measuring device comprising:

an input circuit connected to the induction coil, the input circuit induced a measurement signal corresponding to the induced current;

a sample-hold circuit having a first and second input, the first input receives the measurement signal and is connected to the input circuit, the second input signal receives a timing signal corresponding to the excitation current, wherein the sample-hold circuit holds the measurement signal at a substantially constant value during a hold time period synchronized to the timing signal so as to obtain at least one of the group consisting of: a substantially stable signal and a signal substantially unaffected by effects introduced by a direction change of the alternating excitation current and time-dependent transitions of the measurement signal.

14. The device of claim 13, wherein the hold time period duration is approximately longer than a quarter of the time period of the alternating current.

15. The device of claim 13, further comprising at least one of the group consisting of an A/D converter and a rectifier circuit interposed between the input circuit and the sample hold-circuit so as to convert the measurement signal into one of the group consisting of: a voltage, a digitalized signal, a rectified signal, and a synchronous rectified signal.

16. The device of claim 13, further comprising a current source connected to the excitation coil.

17. A measuring system comprising a measuring device according to claim 13, said measuring system comprising an inductive conductivity sensor immersed in the fluid medium in communication with said input circuit, wherein the excitation coil and the induction coil are carried by at least one toroidal core, wherein the toroidal core is selected from the group consisting of: a ferrite ring or a magnetic ring.

* * * * *